(12) United States Patent
Zhang et al.

(10) Patent No.: US 12,415,740 B1
(45) Date of Patent: Sep. 16, 2025

(54) *ASPERGILLUS* SP. DH4 WITH AEROBIC DENITRIFICATION ENHANCED BY INORGANIC ELECTRON DONOR AND USE THEREOF

(71) Applicant: Xi'an University of Architecture and Technology, Xi 'an (CN)

(72) Inventors: Haihan Zhang, Xi 'an (CN); Ben Ma, Xi 'an (CN); Sixuan Pan, Xi 'an (CN); Fengrui Li, Xi 'an (CN)

( * ) Notice: Subject to any disclaimer, the term of this patent is extended or adjusted under 35 U.S.C. 154(b) by 0 days.

(21) Appl. No.: 19/069,227

(22) Filed: Mar. 4, 2025

(30) Foreign Application Priority Data

Mar. 14, 2024 (CN) .......................... 202410288115.9

(51) Int. Cl.
| | | |
|---|---|---|
| C02F 3/34 | (2023.01) | |
| C02F 3/02 | (2023.01) | |
| C12N 1/14 | (2006.01) | |
| C02F 101/16 | (2006.01) | |
| C02F 103/00 | (2006.01) | |
| C12R 1/66 | (2006.01) | |

(52) U.S. Cl.
CPC ................ *C02F 3/346* (2013.01); *C02F 3/02* (2013.01); *C02F 3/348* (2013.01); *C12N 1/145* (2021.05); *C02F 2101/163* (2013.01); *C02F 2103/007* (2013.01); *C12R 2001/66* (2021.05)

(58) Field of Classification Search
None
See application file for complete search history.

(56) References Cited

FOREIGN PATENT DOCUMENTS

| | | |
|---|---|---|
| CN | 110669674 A | 1/2020 |
| CN | 117417838 A | 1/2024 |

*Primary Examiner* — Chester T Barry

(57) ABSTRACT

An *Aspergillus* sp. DH4 with aerobic denitrification enhanced by an inorganic electron donor and its application are provided, which relates to the field of microbial technologies. The *Aspergillus* sp. DH4 is preserved at China Center for Type Culture Collection (CCTCC), a preservation address is Wuhan University, 299 Bayi Road, Wuchang District, Wuhan City, China, a preservation number is CCTCC NO: M20232690, and a preservation date is Dec. 27, 2023.

6 Claims, 22 Drawing Sheets

Specification includes a Sequence Listing.

| Condition | | Zero-order model | | Half-order model | | First-order model | |
|---|---|---|---|---|---|---|---|
| | | $K_{0,VR}(mg^{-1})$ | $R^2$ | $K_{½,VR}(mg^{½}(L^3·h)^{-½})$ | $R^2$ | $K_{1,VR}(h^{-1})$ | $R^2$ |
| C/N ratio | 1 | 0.3695 | 0.9095 | 0.1169 | 0.8833 | 0.1347 | 0.8099 |
| | 1.5 | 0.3777 | 0.9030 | 0.1235 | 0.8971 | 0.1442 | 0.8253 |
| | 2 | 0.3749 | 0.8935 | 0.1299 | 0.9794 | 0.1601 | 0.9459 |
| | 2.5 | 0.3897 | 0.8871 | 0.1354 | 0.9265 | 0.1615 | 0.9386 |
| rotation speed | 40 | 0.2561 | 0.9606 | 0.0694 | 0.9233 | 0.0740 | 0.8780 |
| | 80 | 0.2982 | 0.9868 | 0.0849 | 0.9466 | 0.0947 | 0.8949 |
| | 120 | 0.3749 | 0.8935 | 0.1299 | 0.9794 | 0.1601 | 0.9459 |
| | 160 | 0.3808 | 0.9248 | 0.1276 | 0.9410 | 0.1517 | 0.8736 |
| Temperature | 5 | 0.1284 | 0.4478 | 0.0320 | 0.5508 | 0.0319 | 0.6142 |
| | 10 | 0.1489 | 0.9367 | 0.0373 | 0.9534 | 0.0372 | 0.9611 |
| | 15 | 0.1776 | 0.9869 | 0.0453 | 0.9874 | 0.0461 | 0.9789 |
| | 20 | 0.2365 | 0.9184 | 0.0788 | 0.9737 | 0.0872 | 0.9365 |

FIG. 9

ASPERGILLUS SP. DH4 WITH AEROBIC DENITRIFICATION ENHANCED BY INORGANIC ELECTRON DONOR AND USE THEREOF

CROSS-REFERENCE TO RELATED APPLICATION

This application claims priority to Chinese Patent Application No. 202410288115.9, filed Mar. 14, 2024, which is herein incorporated by reference in its entirety.

TECHNICAL FIELD

The disclosure relates to the field of microbial technologies, and more particularly to an *Aspergillus* sp. DH4 with aerobic denitrification enhanced by an inorganic electron donor and its use.

STATEMENT REGARDING SEQUENCE LISTING

The sequence listing associated with this application is provided in text format in lieu of a paper copy and is hereby incorporated by reference into the specification. The name of the XML file containing the sequence listing is 25002MYZ-USP1-SL.xml. The XML file is 2,513 bytes; is created on Feb. 25, 2025; and is being submitted electronically via patent center.

BACKGROUND

Biological nitrogen removal refers to a process of converting, by microorganisms, nitrogen-containing compounds in water into dinitrogen oxide or nitrogen gas through biochemical actions. To date, the biological nitrogen removal has been widely applied in the treatment of nitrogen-polluted water bodies, such as wastewater treatment plants, polluted waterways, source reservoirs, and constructed wetlands. The cost-effectiveness, high efficiency, and environmental friendliness of the biological nitrogen removal have made it a primary mode for nitrogen pollution control in water bodies.

Currently, research on the mechanisms of aerobic denitrification mainly focuses on the theories of co-respiration and denitrification enzyme systems. The co-respiration theory suggests that the redox potential of nitrate is close to that of oxygen ($O_2$). Therefore, an aerobic denitrifying strain can perform nitrate respiration (i.e., aerobic denitrification) concurrently with aerobic respiration. Compared to traditional anaerobic denitrification, the aerobic denitrification can simultaneously carry out nitrification and denitrification processes under the same dissolved oxygen conditions. The aerobic denitrifying strain is a key microorganism in the processes of simultaneous nitrification and denitrification (SND) and partial nitrification-denitrification.

Compared to the traditional anaerobic denitrification, the aerobic denitrification can simultaneously carry out the nitrification and denitrification processes under the same dissolved oxygen conditions. With the development of society and the increasing environmental awareness of humans, the carbon to nitrogen (C/N) ratio in wastewater has decreased, leading to a lack of carbon sources for traditional heterotrophic denitrification. Therefore, mixotrophic denitrification is a new alternative. The mixotrophic denitrification refers to the simultaneous presence of a reduced inorganic electron donor and organic matter in a reaction system, both of which can serve as an electron donor for microbial denitrification. However, there are relatively few reports on the mixotrophic denitrification in the related art.

SUMMARY

Removing nitrogen from water bodies plays a crucial role in controlling eutrophication. Among nitrogen removal technologies for the water bodies, biological nitrogen removal is a highly efficient and cost-effective method.

In order to address deficiencies in the related art, and in response to the above problems, the disclosure aims at providing an *Aspergillus* sp. DH4 with denitrification performance enhanced by iron as an inorganic electron donor.

The *Aspergillus* sp. DH4 with aerobic denitrification enhanced by the inorganic electron donor, is preserved at China Center for Type Culture Collection (CCTCC), a preservation address is Wuhan University, 299 Bayi Road, Wuchang District, Wuhan City, China, a preservation number is CCTCC NO: M20232690 and a preservation date is Dec. 27, 2023.

The *Aspergillus* sp. DH4 is applied in restoring a nitrogen-containing water body. For example, the *Aspergillus* sp. DH4 is added to the nitrogen-containing water body.

In an embodiment, a carbon to nitrogen (C/N) ratio of the nitrogen-containing water body is in a range of 1-2.5, and a temperature of the nitrogen-containing water body is in a range of 25-30 degrees Celsius (° C.). A rotation speed of the nitrogen-containing water body is in a range of 80-120 revolutions per minute (rpm).

In an embodiment, during the restoring a nitrogen-containing water body, a usage amount of the *Aspergillus* sp. DH4 is 1%-5% of the nitrogen-containing water body in percentages by weight.

In an embodiment, the inorganic electron donor is zero-valent iron.

In an embodiment, the zero-valent iron is a zero-valent iron powder or a zero-valent iron rod.

A method for removing nitrate from a polluted water body includes: inoculating the *Aspergillus* sp. DH4 into the nitrogen-containing water body, where the zero-valent iron is added as the inorganic electron donor.

Iron, as the fourth most abundant element in the earth crust, plays a significant role in the biogeochemical cycling of the nitrogen in ecosystems. Utilizing reduced iron as an electron donor for denitrification, the coupling of iron oxidation and nitrogen reduction holds broad application prospects in nitrogen removal from water sources. The addition of the zero-valent iron may involve both chemical and biological denitrification processes. During chemical denitrification, the oxidation of the zero-valent iron releases electrons that serve as electron donors for nitrate reduction. In biological denitrification, the generated ferrous ion ($Fe^{2+}$) may further participate in $Fe^{2+}$-mediated autotrophic denitrification.

Without adding exogenous inorganic electron donors, the *Aspergillus* sp. DH4 has a nitrate removal rate of approximately 30% in a medium with a C/N ratio of 2. The accumulation and subsequent removal of nitrite are observed between days 6 and 10, indicating the occurrence of aerobic denitrification.

The effect of different iron added dosages on the nitrogen removal performance of the *Aspergillus* sp. DH4 is investigated when adding the iron as the inorganic electron donor. To investigate the effect of different iron added dosages on the nitrogen removal performance of the *Aspergillus* sp. DH4, the iron is added at concentrations of 5, 10, 15, and 20 grams per liter (g/L). The removal of nitrate nitrogen ($NO_3^-$—N), ammonia nitrogen ($NH_4^+$—N), nitrite nitrogen ($NO_2^-$—N), and total nitrogen (TN) in the medium with the C/N ratio of 2 by the *Aspergillus* sp. DH4 under different iron added dosages is detected every 2 days.

As the added dosage of iron increases, the nitrate removal rate of the *Aspergillus* sp. DH4 gradually accelerates, with complete nitrate removal achievable within 6 days at a highest added dosage. However, the accumulation of the $NH_4^+$—N also increases continuously, indicating that the proportion dominated by the chemical action of the iron is gradually increasing.

The optimal added dosage of the iron as the inorganic electron donor for the denitrification of the *Aspergillus* sp. DH4 is determined. Based on the analysis of experimental results, the iron added dosage of 10 g/L is selected as the optimal added dosage, which achieves a relatively fast nitrate removal rate with minimal accumulation of the $NH_4^+$—N, which could ultimately be removed through nitrification.

Compared to the related art, the disclosure has the following beneficial effects.

The disclosure obtains the *Aspergillus* sp. DH4 with the aerobic denitrification performance enhanced by the iron as the inorganic electron donor. The *Aspergillus* sp. DH4 with the aerobic denitrification enhanced by the inorganic electron donor is preserved at CCTCC, a preservation address is Wuhan University, 299 Bayi Road, Wuchang District, Wuhan City, China, a preservation number is CCTCC NO: M20232690 and a preservation date is Dec. 27, 2023. When performing aerobic denitrification not enhanced by the iron as the inorganic electron donor, the *Aspergillus* sp. DH4 achieves a nitrate removal rate of approximately 30% in a medium with a C/N ratio of 2. The addition of 20 g/L iron allows for complete nitrate removal by the sixth day. When 10 g/L of the iron is added, the nitrate removal rate is faster, and there is less accumulation of the $NH_4^+$—N, making it the optimal added dosage. Valuable reference for the denitrification performance of aerobic denitrifying strains enhanced by inorganic electron donors is provided.

BRIEF DESCRIPTION OF DRAWINGS

FIG. 2B corresponds to a case at 80 rpm; FIG. 2C corresponds to a case at 120 rpm; and FIG. 2D corresponds to a case at 160 rpm.

FIG. 3B corresponds to a case at C/N=1.5; and FIG. 3C corresponds to a case at C/N=2.5.

FIG. 4A represents concentration changes of $NO_3^-$—N; FIG. 4B represents concentration changes of $NO_2^-$—N; FIG. 4C represents concentration changes of $NH_4^+$—N; and FIG. 4D represents concentration changes of TN.

FIG. 5B corresponds to a case at a temperature of 10° C.; FIG. 5C corresponds to a case at a temperature of 15° C.; and FIG. 5D corresponds to a case at a temperature of 20° C.

FIG. 9 illustrates kinetic models for nitrate removal under different parameters for the *Aspergillus* sp. DH4 of the disclosure.

DETAILED DESCRIPTION OF EMBODIMENTS

Figure 1A:
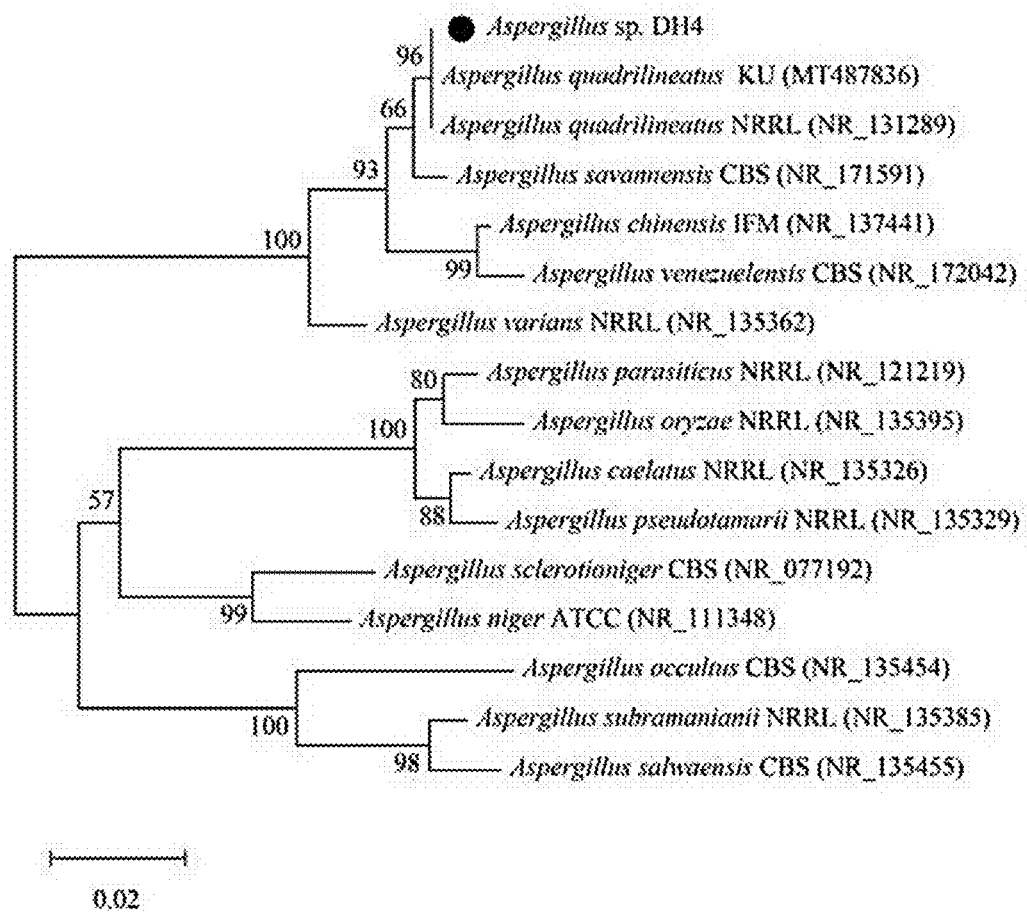
FIG. 1A and FIG. 1B respectively illustrate a phylogenetic tree and strain morphology of an *Aspergillus* sp. DH4 of the disclosure.
Figure 1B:
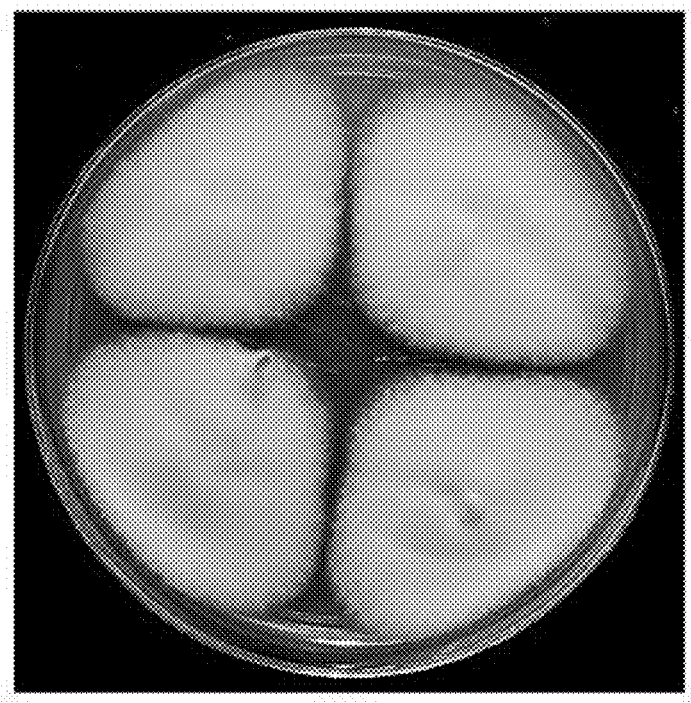
Figure 2A:
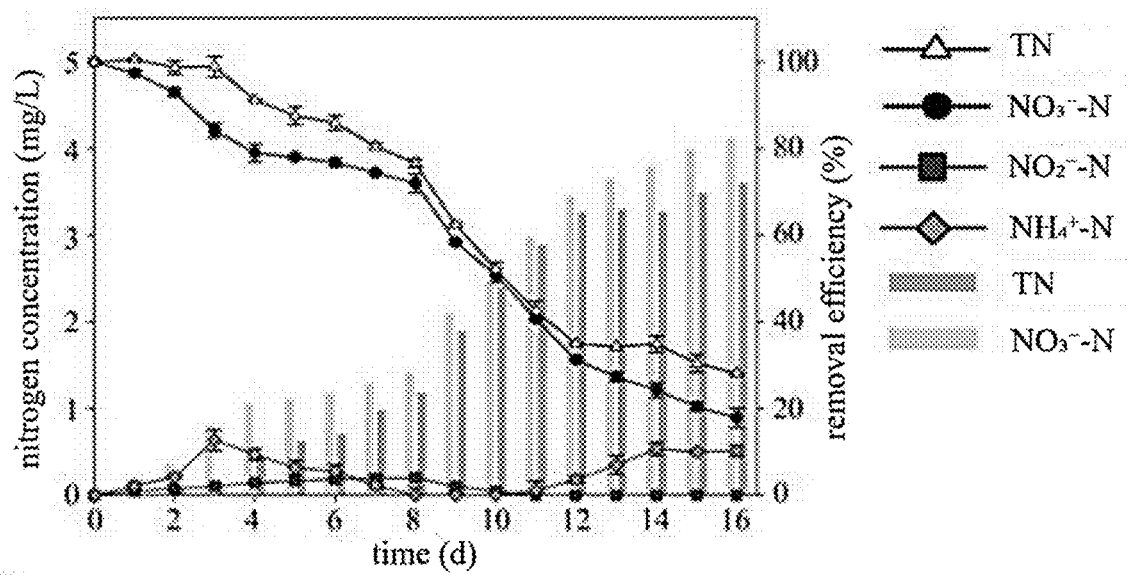
FIGS. 2A-2D respectively illustrate schematic diagrams of nitrogen removal performance of the *Aspergillus* sp. DH4 of the disclosure at different rotation speeds; where FIG. 2A corresponds to a case at 40 rpm.
Figure 2B:
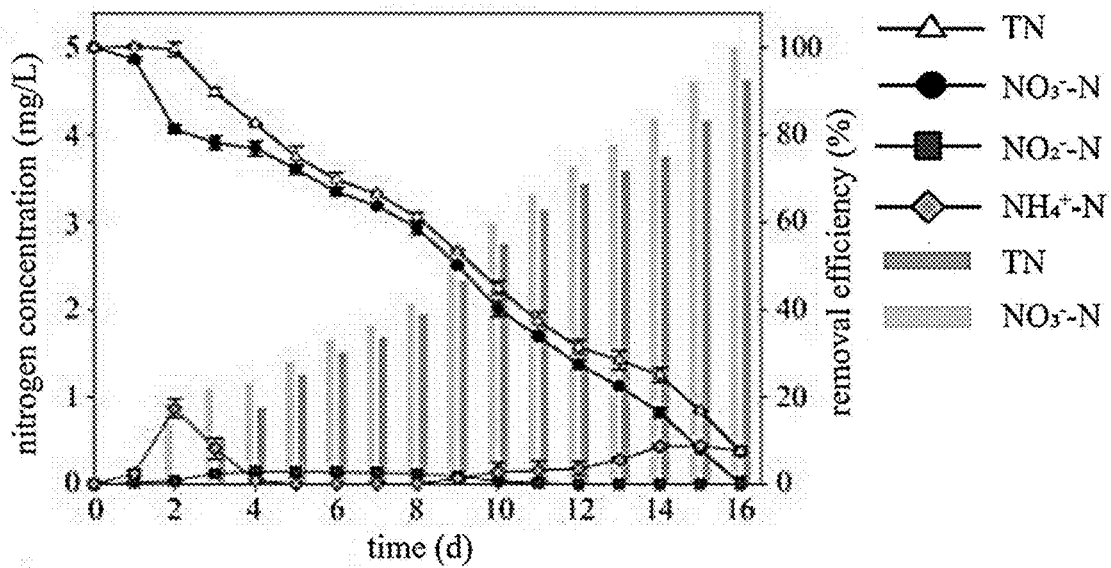
Figure 2C:
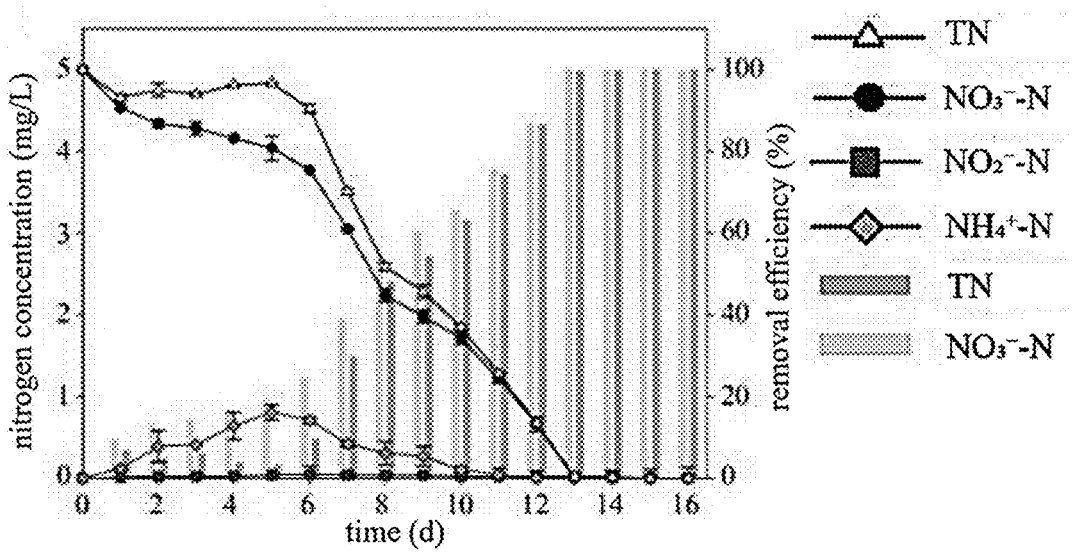
Figure 2D:
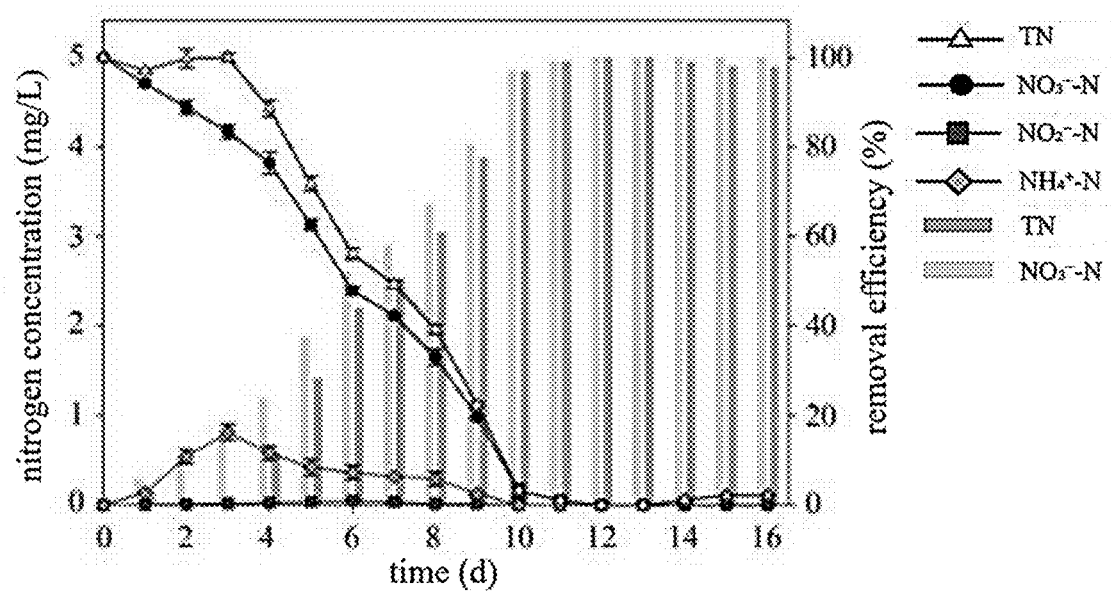

The embodiments of the disclosure are described in detail below, but it should be understood that the scope of protection of the disclosure is not limited by the illustrated embodiments. Based on the embodiments of the disclosure, all other embodiments obtained by those skilled in the art without creative labor are within the scope of protection of the disclosure. The experimental methods described in each embodiment of the disclosure are conventional methods unless otherwise specified.

A rose Bengal agar medium includes a formulation consisting of: 5 g/L of peptone, 0.025 g/L of $C_{20}H_2Cl_4I_4Na_2O_5$ (rose Bengal), 10 g/L of $C_6H_{12}O_6$ (glucose), 0.002 g/L of $C_6H_4Cl_2N_2O_2$ (4,5-dichloro-2-nitroaniline), 1 g/L of $KH_2PO_4$ (potassium dihydrogen phosphate), 0.1 g/L of $C_{11}H_{12}Cl_2N_2O_5$ (chloramphenicol), and 0.5 g/L of $MgSO_4$ (magnesium sulfate), with a pH in a range of 5.6-5.8; and 20 g/L of agar powder is added to the formulation to prepare a fungal solid medium.

A denitrification liquid medium (DM) uses a conventional denitrification liquid medium known in the related art, with a formulation and a preparation method including: 0.108 g/L of $KNO_3$ (potassium nitrate), 1.5 g/L of $KH_2PO_4$, 0.413 g/L of glucose, 0.1 g/L of $MgSO_4 \cdot 7H_2O$ (magnesium sulfate heptahydrate), 5.0 g/L of $Na_2HPO_4 \cdot 12H_2O$ (disodium hydrogen phosphate dodecahydrate), and 2 milliliters (mL) of trace element stock solution are added to ultrapure water followed by adjusting a volume to 1 liter (L) and stirring until completely dissolved to obtain first mixed solution, a pH of the first mixed solution is adjusted to 7.0-7.2, and then the first mixed solution is sterilized at 121° C. for 30 minutes (min) and stored for later use.

A formulation and a preparation method of the trace element stock solution are as follows. 4.4 milligrams (mg) of $ZnSO_4$ (zinc sulfate), 100 mg of ethylene diamine tetraacetic acid (EDTA), 10.2 mg of $MnCl_2 \cdot 4H_2O$ (manganese(II) chloride tetrahydrate), 11 mg of $CaCl_2$ (calcium chloride), 10 mg of $FeSO_4 \cdot 7H_2O$ (ferrous sulfate heptahydrate), 3.2 mg of $CuSO_4 \cdot 5H_2O$ (copper(II) sulfate pentahydrate), 2.2 mg of $(NH_4)_6Mo_7O_{24} \cdot 4H_2O$ (ammonium molybdate tetrahydrate), and 3.2 mg of $CoCl_2 \cdot 6H_2O$ (cobalt(II) chloride hexahydrate) are added to ultrapure water followed by adjusting a volume to 1 L, and stirring until completely dissolved to obtain second mixed solution, a pH of the second mixed solution is adjusted to 7.0-7.2, and then the second mixed solution is sterilized at 121° C. for 30 min and stored for later use.

In the disclosure, the term "iron" refers to zero-valent iron, which can be in a form of an iron powder or an iron rod. The unit "g/L" for iron added dosage indicates grams of the iron added per liter of treated water.

In a fungal suspension of an *Aspergillus* sp. DH4 with a weight concentration of 1%, there are approximately $5 \times 10^5$ cells.

Embodiment 1

Strain isolation and purification are as follows.

Denitrifying fungal strains are enriched and isolated from overlying water samples of a water source reservoir.

Fresh sediment and floating water samples are collected from Xili Reservoir in Shenzhen, China, located at 113° 57'6" east (E), and 22° 35'37" north (N), with a sampling depth of 0-0.5 meters (m). In this experiment, the water and sediment are placed in a beaker of 2 L followed by continuous aerating to maintain a dissolved oxygen concentration of 6.6 milligrams per liter (mg/L). After one month of continuous aerobic acclimatization, supernatant of the water sample in the beaker is extracted, and then diluted by using a 10-fold serial dilution method, followed by being coated onto rose Bengal agar mediums to obtain coated plates.

The coated plates are inverted and incubated in a biochemical incubator at 30° C. until visible colonies formed, with each mixed microbial sample coated on three plates. All materials used are sterilized at 121° C. for 30 min and then operated in a sterile clean bench. After colony formation, plate coating is repeated 3-5 times until distinct single colonies are obtained.

A strain obtained from the single colonies is subjected to internal transcribed spacer (ITS) sequencing to obtain its genetic information.

The strain is identified as *Aspergillus* sp. (a species within the genus *Aspergillus*), and named DH4. The colonies of the strain appear white and radiating. The phylogenetic tree of the *Aspergillus* sp. DH4 is constructed by using the neighbor-joining method. *Aspergillus quadrilineatus* KU and *Aspergillus quadrilineatus* NRRL show a genetic sequence similarity of over 99% with the *Aspergillus* sp. DH4, indicating that the strain DH4 belongs to the genus *Aspergillus*. A length of the ITS gene of the *Aspergillus* sp. DH4 is 533 base pairs (bp), and the sequence of the *Aspergillus* sp. DH4 is

```
CTGCGGAAGGATCATTACCGAGTGCGGGCTGCCTCCGGGCGCCCAACCT

CCCACCCGTGACTACCTAACACTGTTGCTTCGGCGGGGAGCCCCCTAGG

GGCGAGCCGCCGGGGACCACTGAACTTCATGCCTGAGAGTGATGCAGTC

TGAGCCTGAATACAAATCAGTCAAAACTTTCAACAATGGATCTCTTGGT

TCCGGCATCGATGAAGAACGCAGCGAACTGCGATAAGTAATGTGAATTG

CAGAATTCAGTGAATCATCGAGTCTTTGAACGCACATTGCGCCCCTGG

CATTCCGGGGGCATGCCTGTCCGAGCGTCATTGCTGCCCTCAAGCCCG

GCTTGTGTGTTGGGTCGTCGTCCCCCCCGGGGACGGGCCCGAAAGGCA
```

```
-continued

GCGGCGGCACCGTGTCCGGTCCTCGAGCGTATGGGGCTTTGTCACCCGC

TCGATTAGGGCCGGCCGGGCGCCAGCCGGCGTCTCCAACCTTATTTTTC

TCAGGTTGACCTCGGATCAGGTAGGGATACCCGCTGAACTTAA, denoted as SEQ ID NO: 1.
```

Embodiment 2

Nitrogen removal performance of the *Aspergillus* sp. DH4 with an inorganic electron donor added at different rotation speeds is tested.

The *Aspergillus* sp. DH4 is inoculated into a sterilized DM medium with 5 mg/L of nitrogen and a C/N ratio of 2, and 10 g/L of iron is added as the inorganic electron donor. Then, different rotation speeds of 40, 80, 120, and 160 rpm are set as comparative experiments, and the sterilized DM medium with the *Aspergillus* sp. DH4 inoculated are placed at 30° C. in a biochemical shaker incubator for culturing. Samples are taken every 2 days and filtered through pre-combusted 0.45 micrometers (μm) glass fiber filters (GF/F), and concentrations of $NO_3^-$—N, $NH_4^+$—N, $NO_2^-$—N, and TN are measured under different rotation speeds.

The rotation speed reflects the dissolved oxygen (DO) concentration, and changes of the DO concentration is crucial for the *Aspergillus* sp. DH4 as an aerobic denitrifying strain.

FIGS. 2A-2D show that when the rotation speed is 40 rpm, the nitrate removal rate of the *Aspergillus* sp. DH4 decreases to 82.20%, due to insufficient DO available for the aerobic denitrifying strain, which is unfavorable for denitrification. Meanwhile, the insufficient DO may lead to a reduced oxidation rate of the iron, a decreased supply of electron donors, and consequently, a lower denitrification rate. Moreover, there is some accumulation of $NH_4^+$—N in the later stages of cultivation, reaching up to 0.53 mg/L, which might be caused by the autolysis of dead microbial cells.

FIGS. 2A-2D also indicate that as the rotation speed increases, the nitrogen removal rate of the *Aspergillus* sp. DH4 continuously rises, with the time required to achieve 100% nitrate removal shortening from 16 days to 11 days. This could be attributed to the increased DO concentration, which accelerates mass transfer rates of oxygen and nitrate, and the oxidation rate of the iron, thereby enhancing the activity of nitrogen metabolism enzymes. When examining the iron added dosage, at an iron concentration of 10 g/L, a C/N ratio of 2, a rotation speed of 120 rpm, and a temperature of 30° C., the TN removal rate reaches 100%, and no $NH_4^+$—N accumulation is observed at rotation speeds of 160 rpm and 120 rpm. Throughout the experiment, some accumulation of nitrite is observed at rotation speeds of 40 rpm and 80 rpm, likely due to insufficient DO supply, which reduces the activity of nitrite reductase.

The disclosure selects a rotation speed of 120 rpm as the optimal condition for the *Aspergillus* sp. DH4, and further studies are conducted to investigate factors affecting the nitrogen removal performance of the *Aspergillus* sp. DH4.

Embodiment 3

Nitrogen removal performance of the *Aspergillus* sp. DH4 with an inorganic electron donor added at different C/N ratios is tested.

The *Aspergillus* sp. DH4 with a weight concentration of 1% is inoculated into a sterilized DM medium with 5 mg/L of nitrogen, and 10 g/L of iron is added as the inorganic electron donor; then, the sterilized DM medium with the *Aspergillus* sp. DH4 inoculated are placed in a biochemical shaker incubator at 30° C. and 130 rpm for culturing for 48 hours (h) until a logarithmic growth phase. Different C/N ratios of 1, 1.5, and 2.5 are set as comparative experiments. Samples are taken every 2 days and filtered through pre-combusted 0.45 μm GF/F, and concentrations of $NO_3^-$—N, $NH_4^+$—N, $NO_2^-$—N, and TN are measured under different C/N ratios.

Figure 3A:
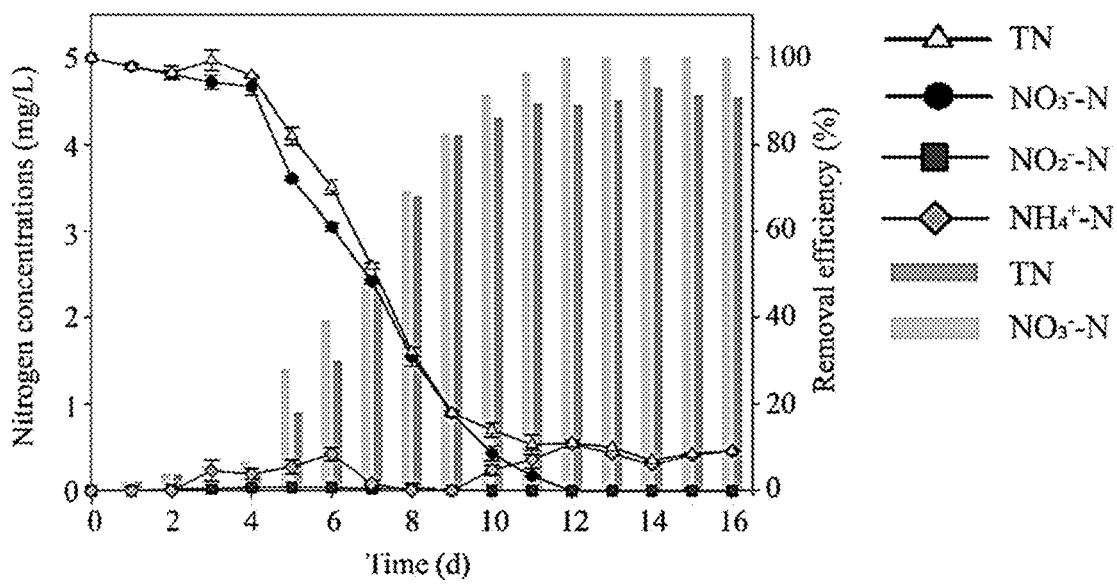
FIGS. 3A-3C respectively illustrate schematic diagrams of the nitrogen removal performance of the *Aspergillus* sp. DH4 of the disclosure at different C/N ratios; where FIG. 3A corresponds to a case at C/N=1.
Figure 3B:
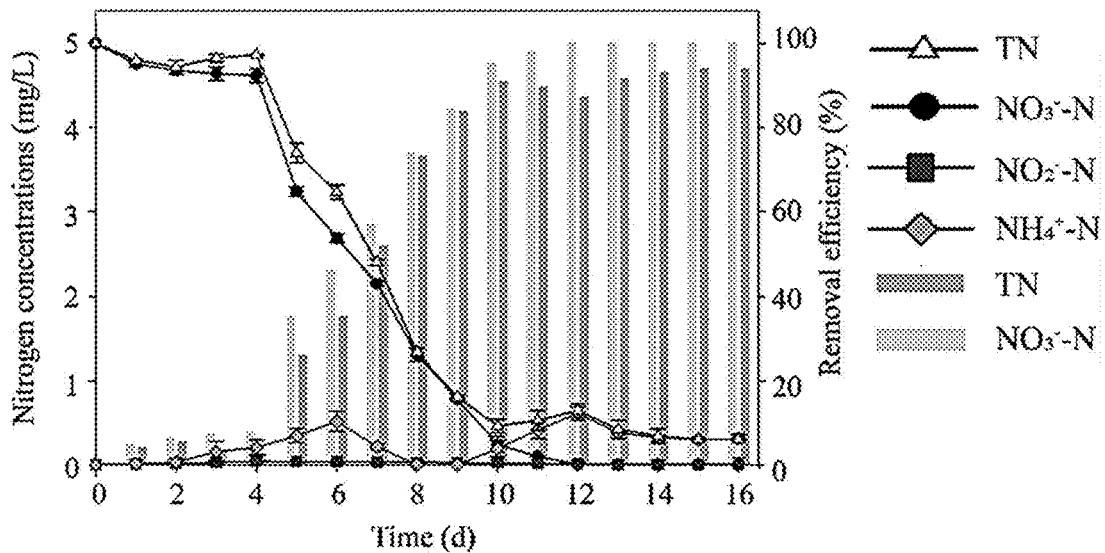
Figure 3C:
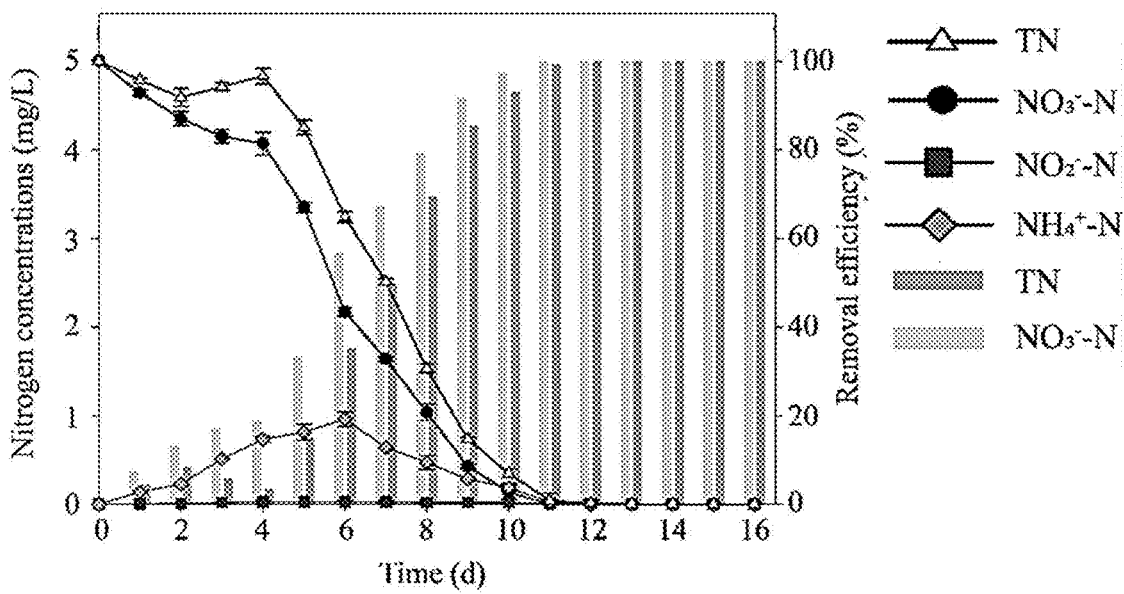
Figure 4A:
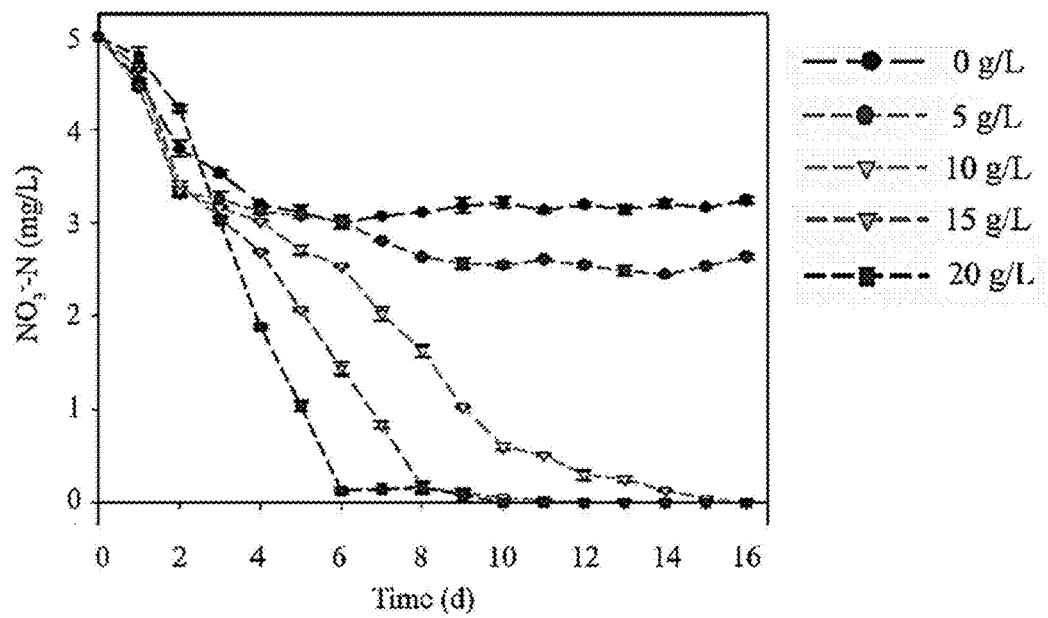
FIGS. 4A-4D respectively illustrate schematic diagrams of the nitrogen removal performance of the *Aspergillus* sp. DH4 of the disclosure at different iron added dosages; where
Figure 4B:
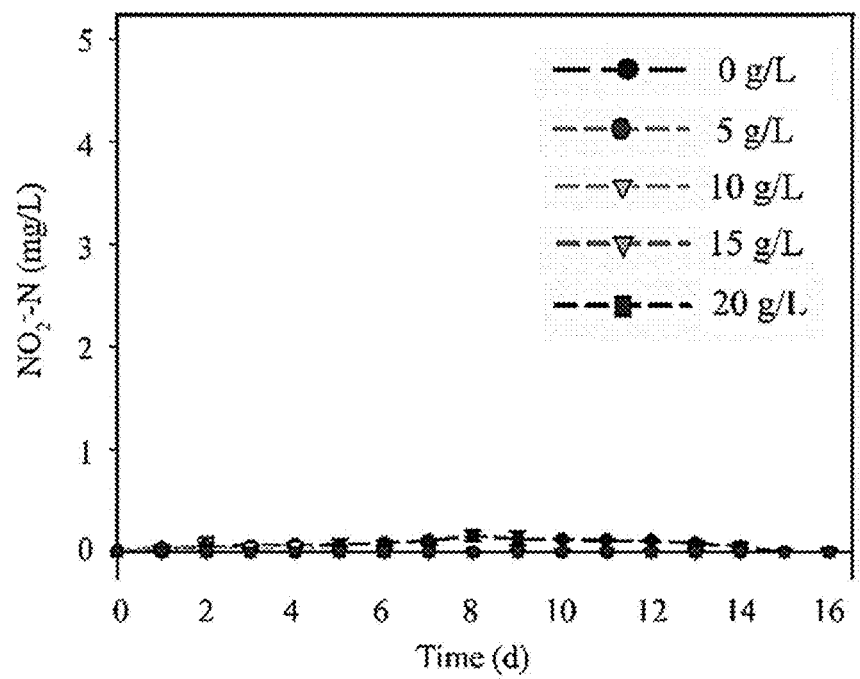
Figure 4C:
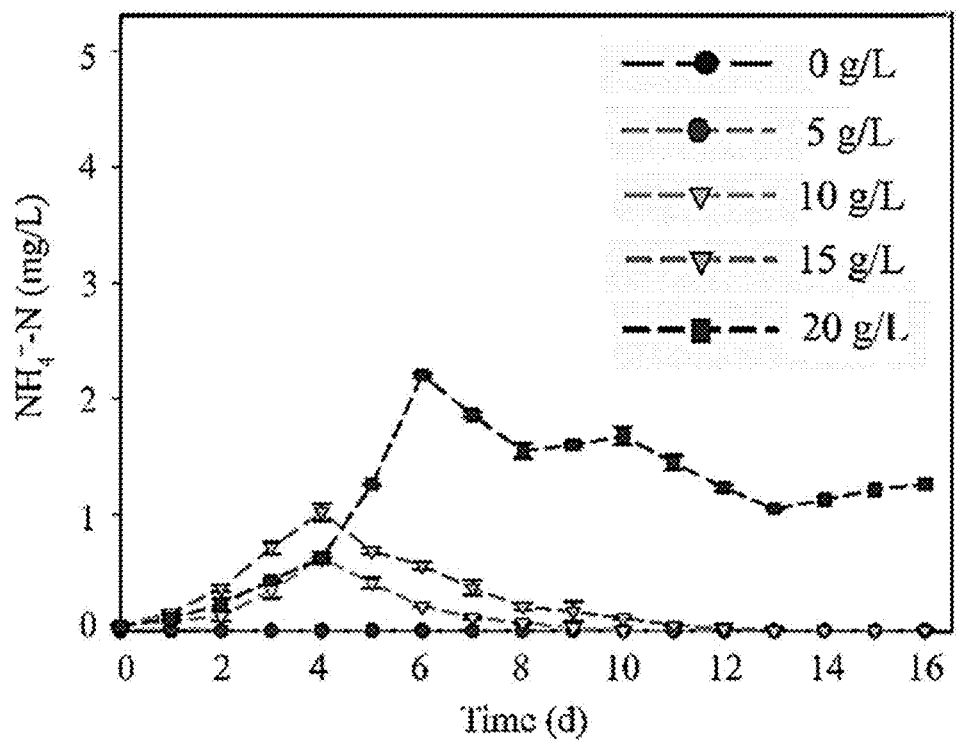
Figure 4D:
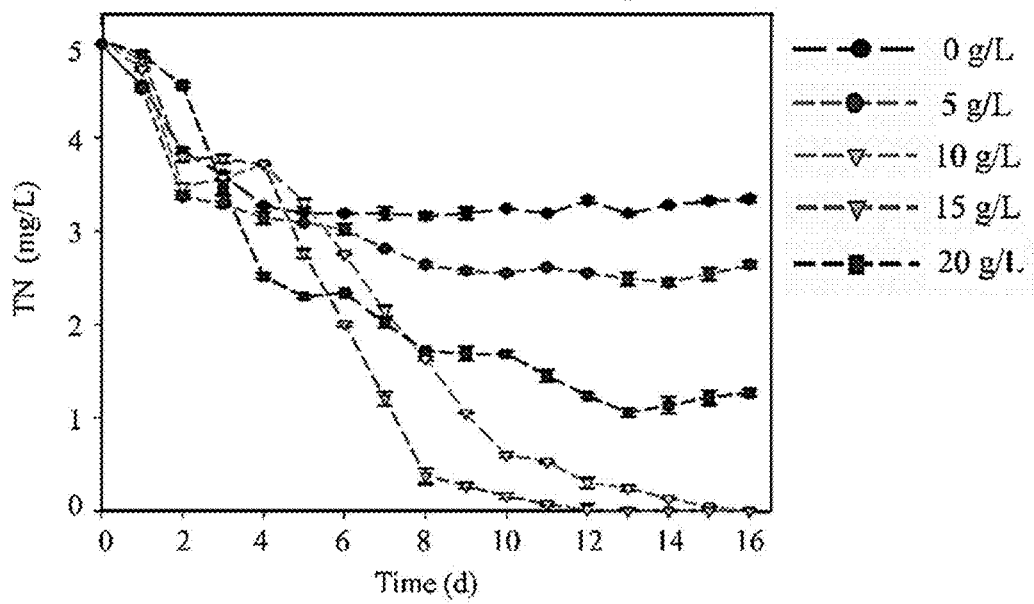
Figure 5A:
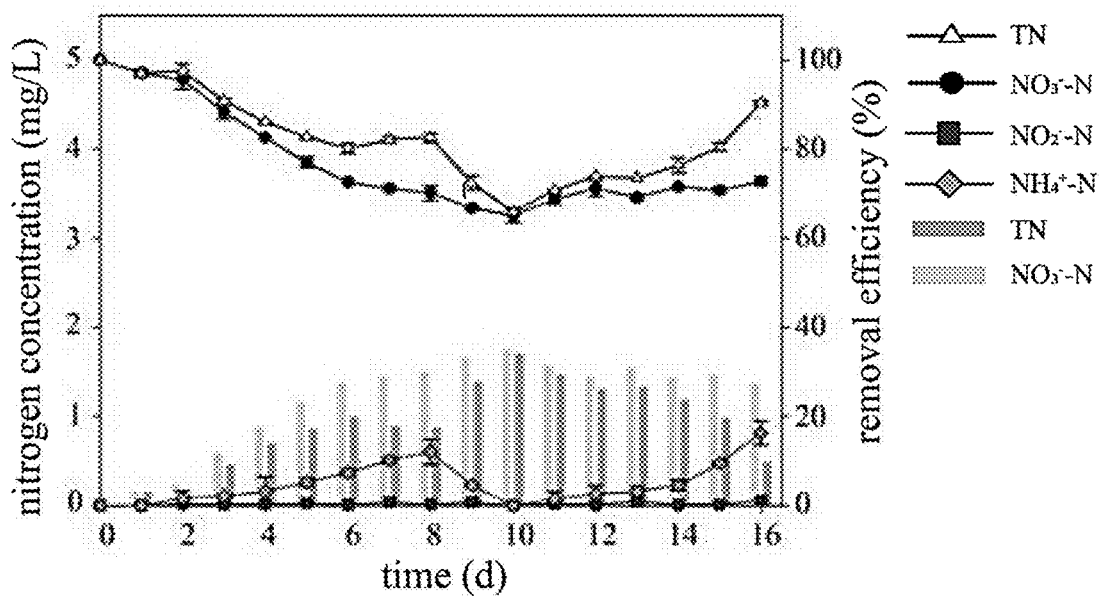
FIGS. 5A-5D respectively illustrate schematic diagrams of the nitrogen removal performance of the *Aspergillus* sp. DH4 of the disclosure at different temperatures; where FIG. 5A corresponds to a case at a temperature of 5° C.
Figure 5B:
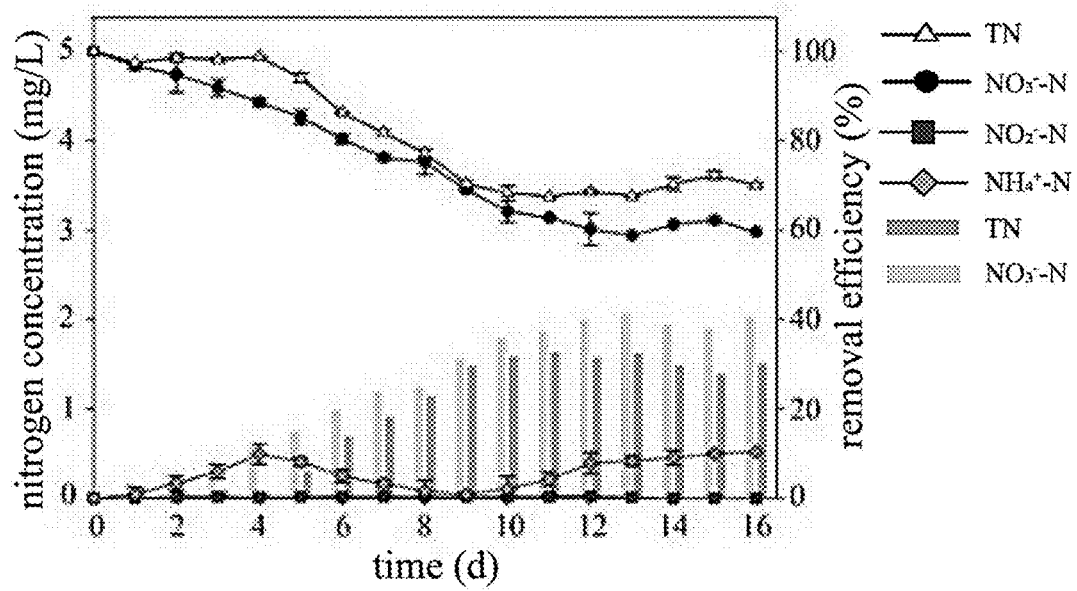
Figure 5C:
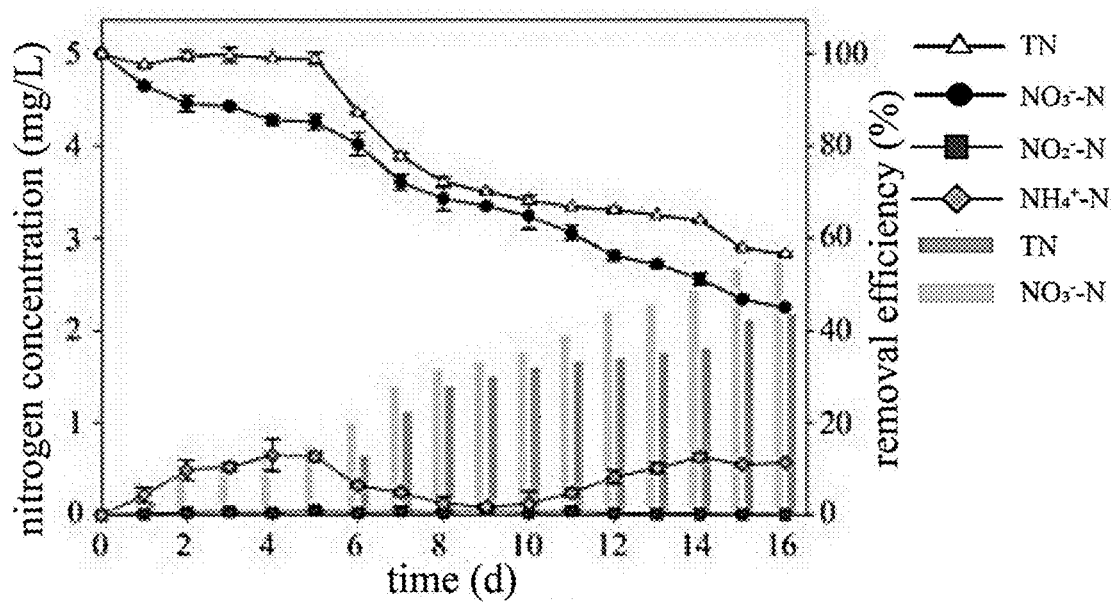
Figure 5D:
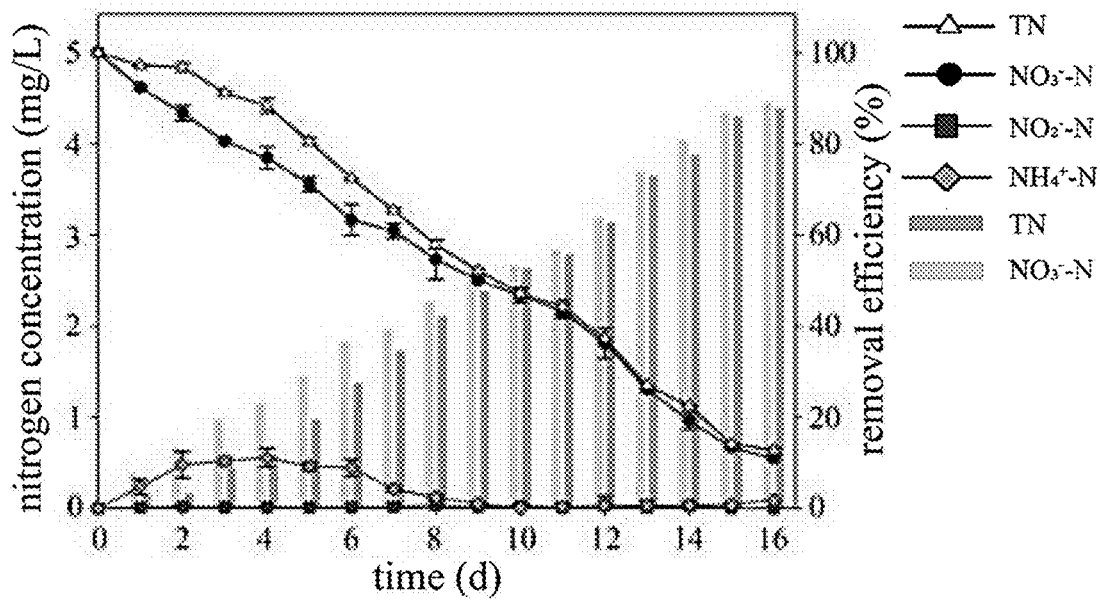
Figure 6A:
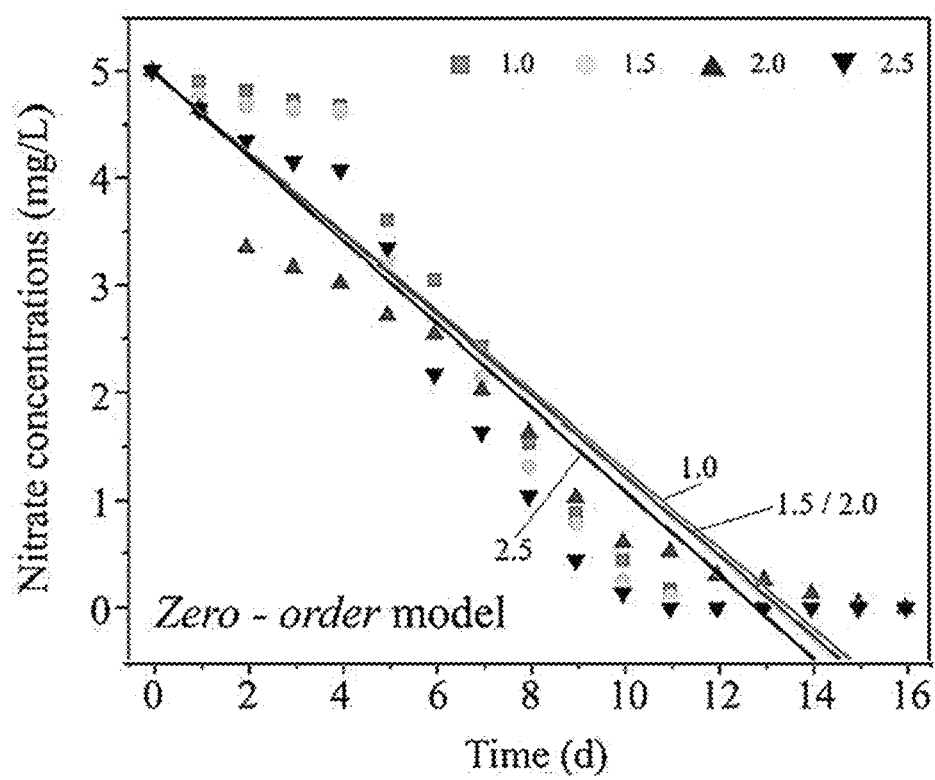
FIGS. 6A-6I respectively illustrate zero-order, half-order, and first-order kinetic models of the *Aspergillus* sp. DH4 at different C/N ratios, different rotation speeds, and different temperatures; where FIGS. 6A-6C respectively represent the zero-order, half-order, and first-order kinetic models at different C/N ratios respectively, FIGS. 6D-6F respectively represent the zero-order, half-order, and first-order kinetic models at different rotation speeds respectively, and FIGS. 6G-6I respectively represent the zero-order, half-order, and first-order kinetic models at different temperatures respectively.
Figure 6B:
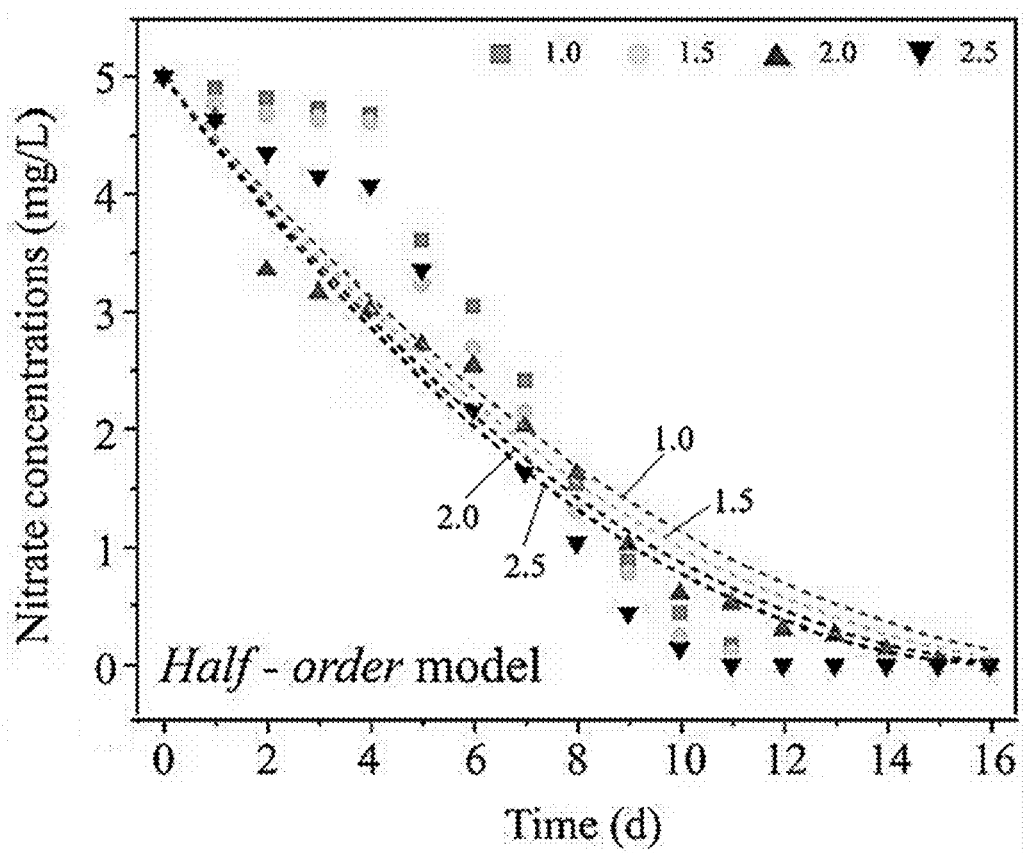
Figure 6C:
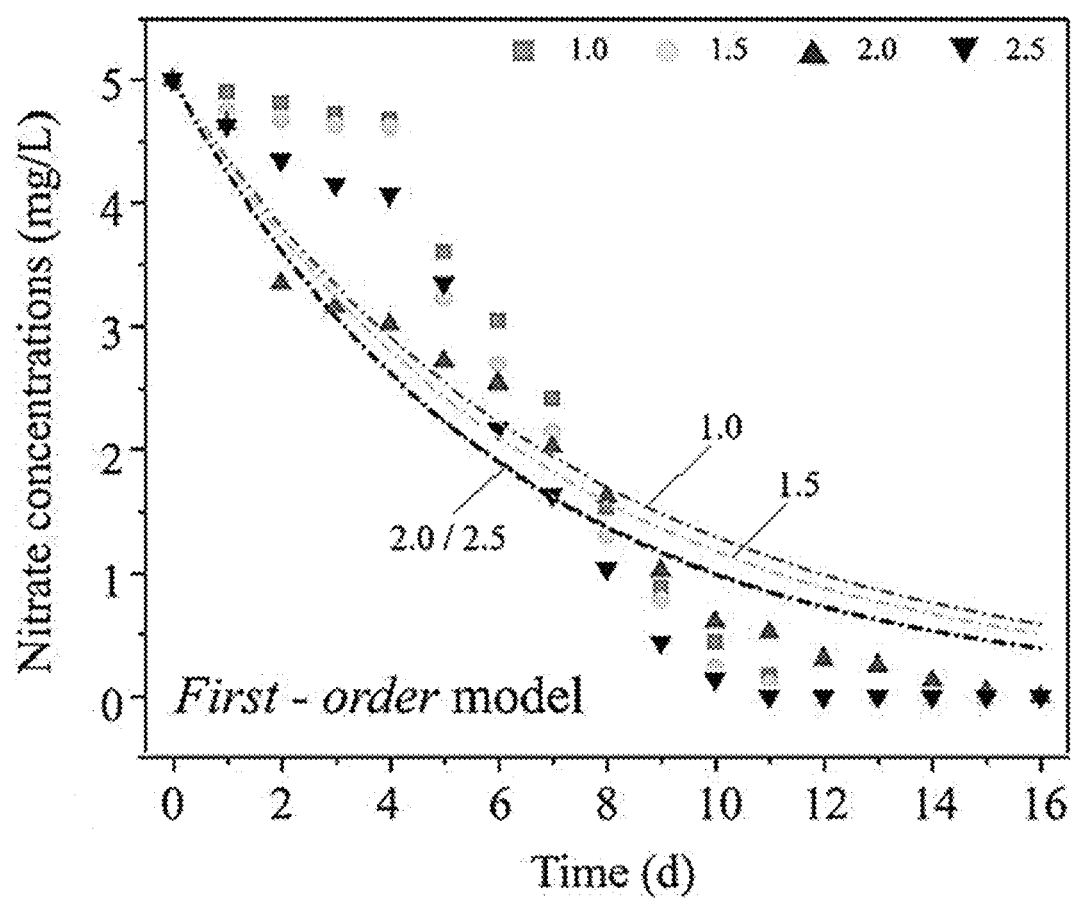
Figure 6D:
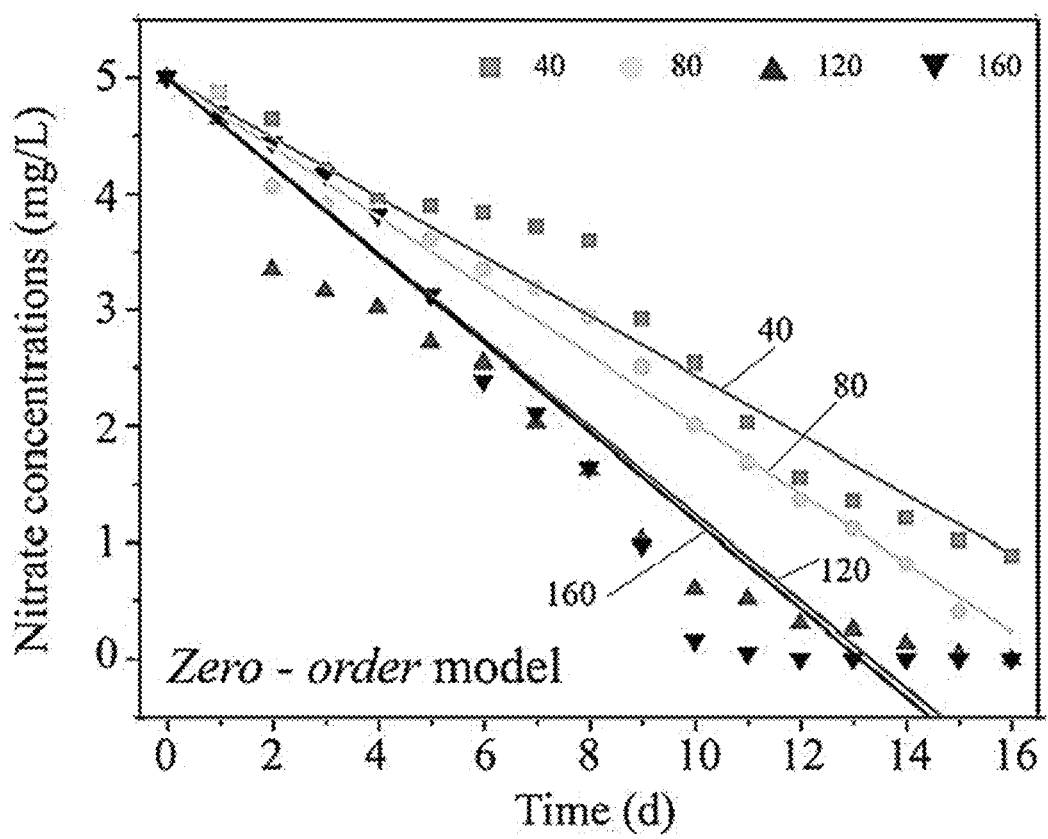
Figure 6E:
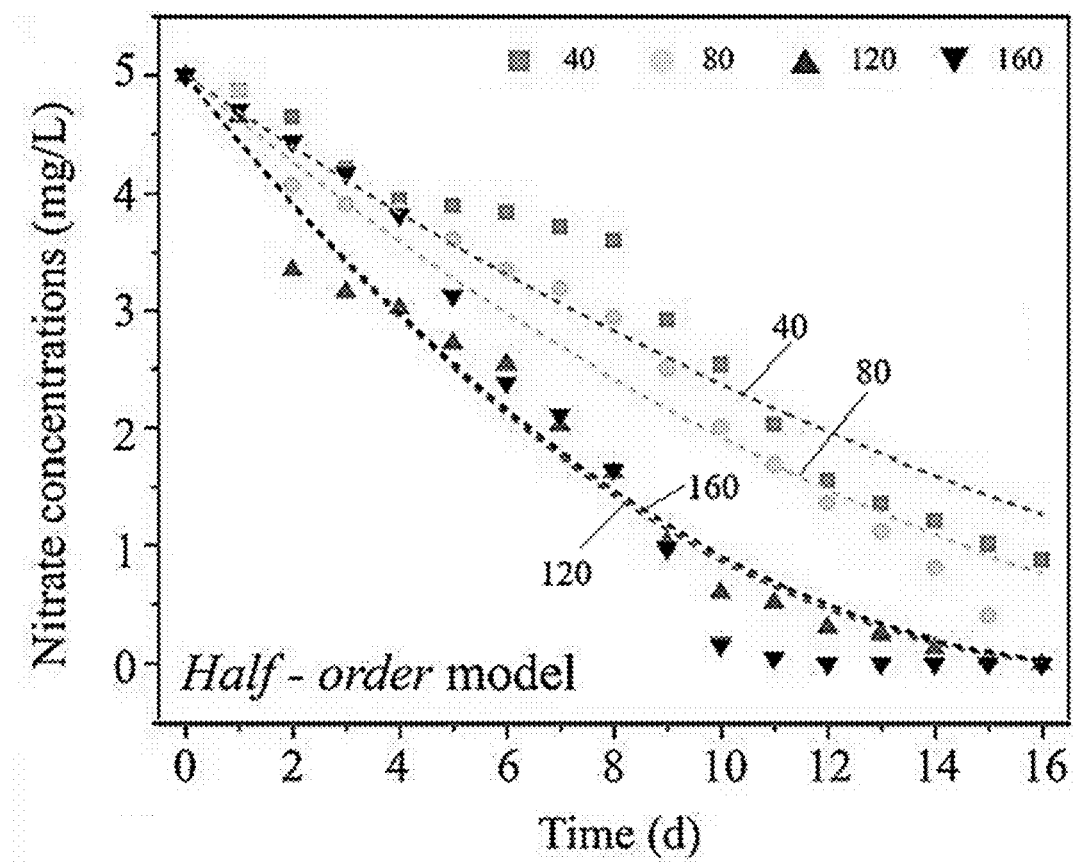
Figure 6F:
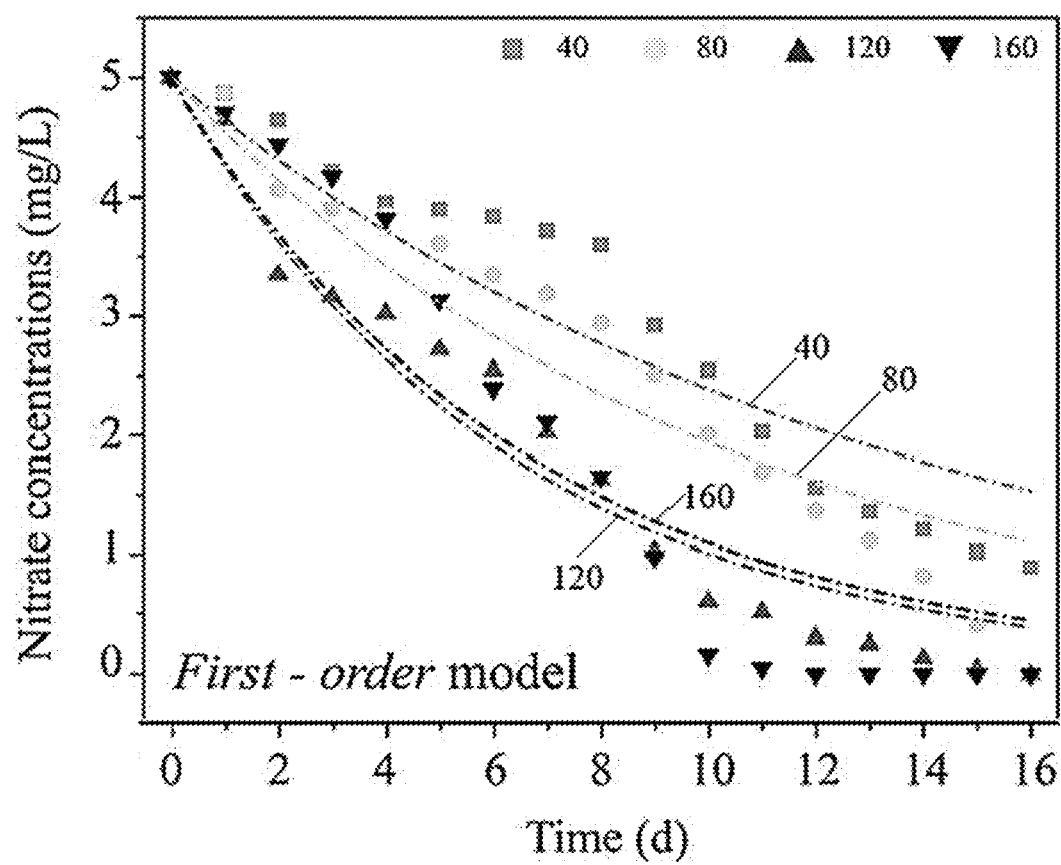
Figure 6G:
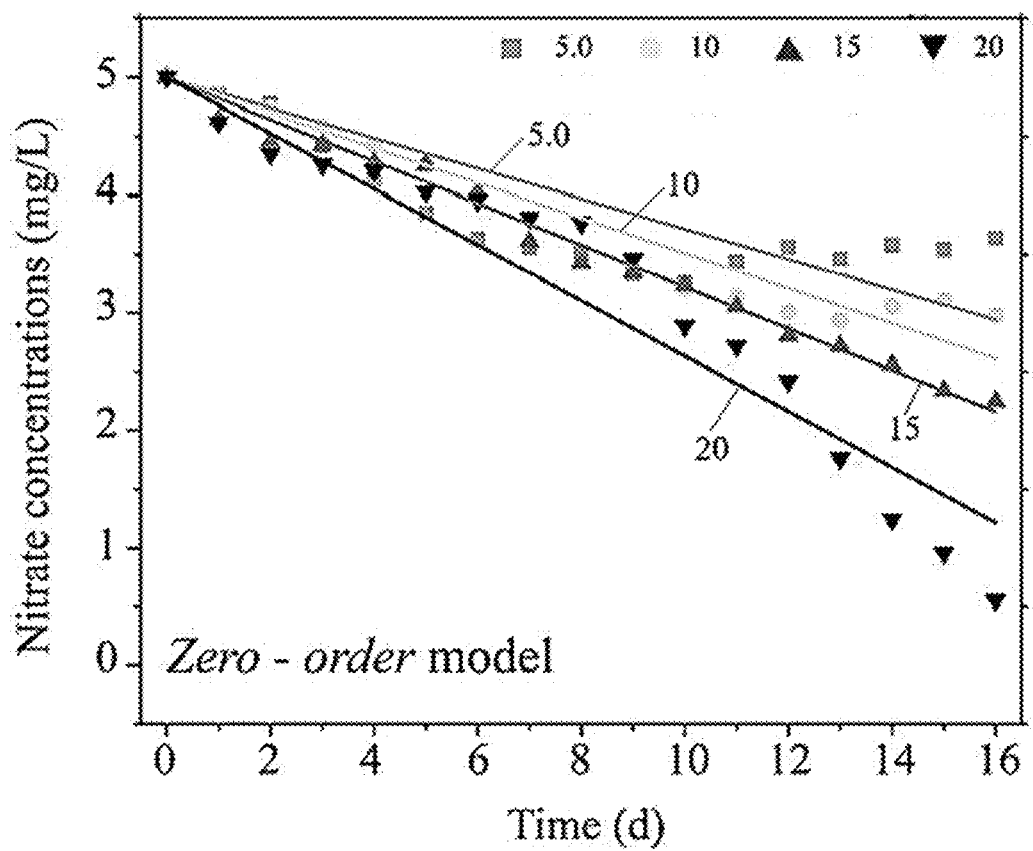
Figure 6H:
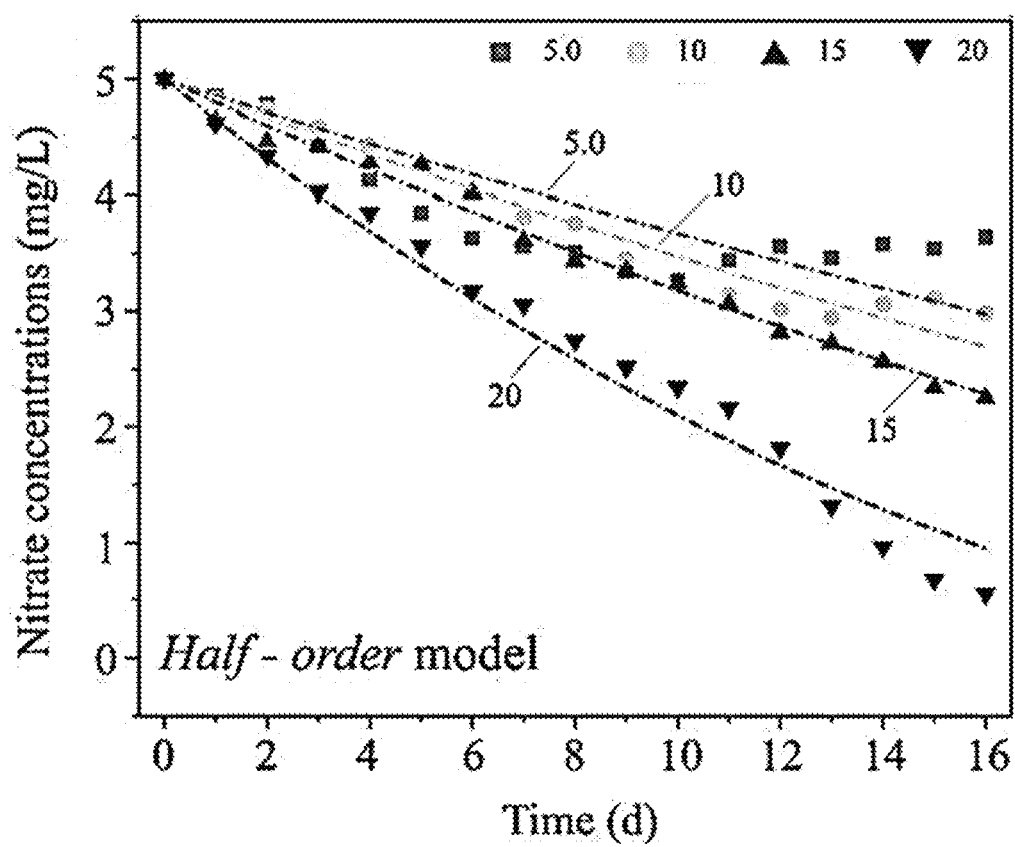
Figure 6I:
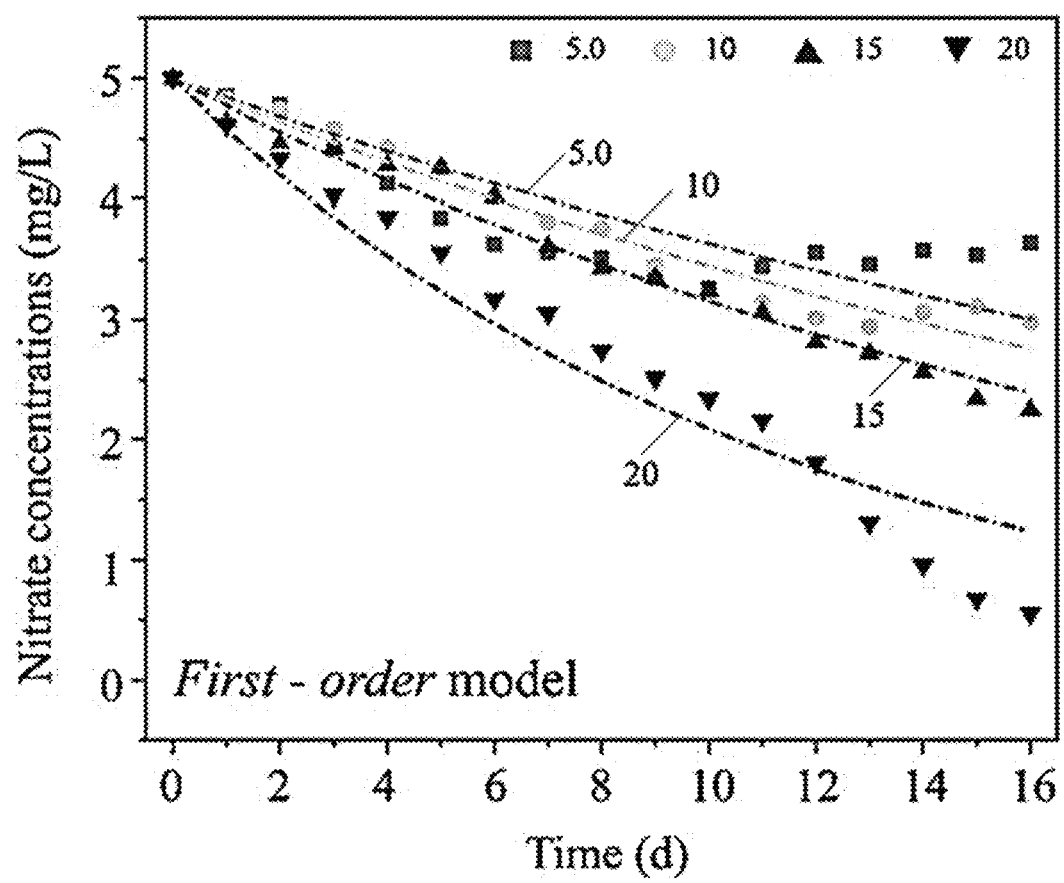

FIGS. 3A-3C show the nitrogen removal rates of the *Aspergillus* sp. DH4 at the C/N ratios of 1, 1.5, and 2.5, examining the effects of different C/N ratios on nitrogen reduction by the *Aspergillus* sp. DH4. When the C/N ratio decreases from 2.5 to 1.5 and 1, the TN removal rate of the *Aspergillus* sp. DH4 decreases from 100% to 90% and 94%, respectively. In each system, the $NO_3^-$—N could be completely removed, but there is a re-accumulation of the $NH_4^+$—N in the later stages of cultivation. This may be due to the release of the $NH_4^+$—N caused by cell death as the cells entered the decline phase, indicating that under low C/N ratios, the limited availability of organic carbon for the *Aspergillus* sp. DH4 may restrict the nitrogen removal performance and cellular activity of the *Aspergillus* sp. DH4.

Under low C/N ratios with the addition of the inorganic electron donor, the *Aspergillus* sp. DH4 could achieve complete TN removal, albeit at different rates. As the C/N ratio increases to 2.5, the TN removal rate of the *Aspergillus* sp. DH4 reaches complete removal by the eleventh day, and there is no further accumulation of the $NH_4^+$—N in the later stages, indicating that increasing the C/N ratio can enhance the TN removal efficiency of the *Aspergillus* sp. DH4.

Considering the actual engineering application scenarios that water source reservoirs are often oligotrophic, the disclosure selects the lower nutrient condition of C/N=2, which can achieve complete nitrogen removal, for further investigation into the factors affecting the nitrogen removal performance of the *Aspergillus* sp. DH4.

Embodiment 4

Nitrogen removal performance of the *Aspergillus* sp. DH4 added with different concentrations of an inorganic electron donor is tested.

The *Aspergillus* sp. DH4 with a weight concentration of 1% is inoculated into a sterilized DM medium with 5 mg/L of nitrogen; then, under conditions of a C/N ratio of 2, a temperature of 30° C. and a rotation speed of 120 rpm, different iron added dosages are set as comparative experiments, and concentrations of $NO_3^-$—N, $NH_4^+$—N, $NO_2^-$—N, and TN are measured under different iron added dosages.

FIGS. 4A-4D show that, without adding iron as the inorganic electron donor, the nitrate removal rate of the *Aspergillus* sp. DH4 in the medium is around 30%. A noticeable accumulation and subsequent removal of nitrite are observed between the sixth day and the tenth day, indicating the occurrence of aerobic denitrification. As the iron added dosage increases, the nitrate removal rate of the *Aspergillus* sp. DH4 gradually accelerates, with a maximum dosage achieving efficient removal within 6 days. Considering the above observations, the iron added dosage of 10 g/L is selected as the optimal iron added dosage, as it achieves a relatively fast nitrate removal rate with minimal accumulation of $NH_4^+$—N that could ultimately be removed through nitrification.

Embodiment 5

Nitrogen removal performance of the *Aspergillus* sp. DH4 with an inorganic electron donor added at different temperatures is tested.

The *Aspergillus* sp. DH4 is inoculated into a sterilized DM medium with 5 mg/L of nitrogen and a C/N ratio of 2, and 10 g/L of iron is added as the inorganic electron donor; then, different temperatures of 5° C., 10° C., 15° C. and 20° C. are set as comparative experiment, and the sterilized DM medium with the *Aspergillus* sp. DH4 inoculated are placed in a biochemical shaker incubator at 120 rpm for culturing. Samples are taken every 2 days and filtered through pre-combusted 0.45 μm GF/F, and concentrations of $NO_3^-$—N, $NH_4^+$—N, $NO_2^-$—N, and TN are measured under different temperatures.

FIGS. 5A-5D show that as the temperature gradually decreases, the TN removal rate of the *Aspergillus* sp. DH4 decreases from 87.3% to 43.48%, 29.96%, and 9.68%. When examining the iron added dosage, at an iron added dosage of 10 g/L, a C/N ratio of 2, a rotation speed of 120 rpm, and a temperature of 30° C., the TN removal rate reaches 100%. The significant decrease in the TN removal rate compared to 30° C. indicates that the *Aspergillus* sp. DH4 is relatively sensitive to temperature changes. Additionally, the re-accumulation of $NH_4^+$—N is observed in the later stages of cultivation under low-temperature conditions, which may be due to the release of $NH_4^+$—N caused by cell death as the cells enter the decline phase, also suggesting lower cellular activity of the *Aspergillus* sp. DH4 at low temperatures.

Considering the overall water level and nitrogen removal situation after reservoir mixing, the disclosure selects 30° C., which brings a higher removal efficiency, as the optimal temperature condition to further investigate the nitrogen removal performance of the *Aspergillus* sp. DH4.

Embodiment 6

Kinetic models for nitrogen removal performance of the *Aspergillus* sp. DH4 under different influencing conditions are obtained.

The disclosure set up changes in three different parameters, including C/N ratio, rotation speed (DO), and temperature, based on the actual seasonal variations (spring, summer, autumn, and winter) and thermal stratification phenomena in the reservoir. To specifically analyze the effects of different conditions on the nitrogen removal performance of the *Aspergillus* sp. DH4, the continuously measured data are fitted into different models. FIGS. 6A-6I show the zero-order, half-order, and first-order kinetic models of the *Aspergillus* sp. DH4 under different C/N ratios, rotation speeds (DO), and temperatures.

FIG. 9 illustrates the kinetic model data for nitrate removal of the *Aspergillus* sp. DH4 under different C/N ratios, rotation speeds (DO), and temperatures.

The zero-order, half-order, and first-order kinetic models are represented by following equations (1), (2), and (3), respectively:

$$C = C_0 - K_{0V,R} T \quad (1)$$

$$C = (C_0^{1/2} - K_{1/2V,R} T)^2 \quad (2)$$

$$C = C_0 \times \exp(-K_{1V,R} T) \quad (3)$$

where C represents a nitrate concentration (mg/L) corresponding to reaction time (T, h), $K_{0V,R}$ (mg/L) represents a reaction rate constant for the zero-order kinetic model, $K_{1/2V,R}$ (mg$^{1/2}$(L$^{1/2}$h)$^{-1}$) represents a reaction rate constant for the half-order kinetic model, and $K_{1V,R}$ (h$^{-1}$) represents a reaction rate constant for the first-order kinetic model.

The equation (1) represents the zero-order kinetic model, which is commonly used to indicate that the reaction rate is not limited by the concentration of the pollutant.

The equation (2) represents the half-order kinetic model, which is commonly used to indicate that environmental factors are the rate-limiting steps in pollutant removal.

The equation (3) represents the first-order kinetic model, which is commonly used to indicate that the environmental factors are the rate-limiting steps in pollutant removal, and the nitrate concentration becomes the limiting factor for the reaction rate.

FIGS. 6A-6I and FIG. 9 show that as the C/N ratio increases, $R^2$ values for the half-order kinetic model ($R^2=0.8833$ at C/N=1.0, $R^2=0.9794$ at C/N=2.0) and the first-order kinetic model ($R^2=0.8099$ at C/N=0.5, $R^2=0.9459$ at C/N=2.0) gradually increase. The maximum coefficients corresponding to the half-order and first-order kinetic models appear at a C/N ratio of 2.5, with values of 0.1354 mg$^{1/2}$(L$^{1/2}$h)$^{-1}$ and 0.1615 h$^{-1}$, respectively. As the C/N ratio increases, the denitrification rate continues to accelerate.

FIGS. 6A-6I and FIG. 9 also show that the *Aspergillus* sp. DH4 fits the half-order kinetic model better under varying rotation speed (rpm) conditions. As the rotation speed increases, the $R^2$ value for the half-order model gradually increases ($R^2=0.9233$ at 40 rpm, $R^2=0.9794$ at 120 rpm), with the maximum coefficient at 120 rpm being 0.1299 mg$^{1/2}$(L$^{1/2}$h)$^{-1}$. This indicates that as the rotation speed increases, the denitrification rate accelerates. However, in the half-order kinetic model, when the rotation speed increases to 160 rpm, the $R^2$ value decreases from 0.9794 to 0.9410, and the denitrification rate decreases to some extent. This suggests that excessively high DO levels can hinder mass transfer rates, thereby reducing the denitrification rate.

FIGS. 6A-6I and FIG. 9 further show that the *Aspergillus* sp. DH4 fits the half-order kinetic model better under varying temperature conditions. As the temperature increases, the $R^2$ value for the half-order model gradually increases ($R^2=0.5508$ at 5° C., $R^2=0.9737$ at 20° C.), with the maximum coefficient at 20° C. being 0.0788 mg$^{1/2}$(L$^{1/2}$h)$^{-1}$. This indicates that as the temperature increases, the denitrification rate accelerates.

Under varying conditions of C/N ratio, rotation speed and temperature, the denitrification rate fits the half-order rate equation better, indicating that the reaction rate is influenced by external environmental conditions. Changes in external conditions may also affect the release of $Fe^{3+}$, thereby influencing the denitrification rate. Therefore, under natural conditions, these environmental factors do not affect the nitrate removal of the *Aspergillus* sp. DH4 individually but rather collectively.

Embodiment 7

The nitrogen removal performance, and cell growth and DOC removal of the *Aspergillus* sp. DH4 under optimal conditions are obtained.

The *Aspergillus* sp. DH4 is inoculated into a sterilized DM medium with 5 mg/L of nitrogen and a C/N ratio of 2, and 10 g/L of iron is added as the inorganic electron donor; then, the sterilized DM medium are placed in a biochemical shaker incubator at 30° C. and 120 rpm for culturing. Samples are taken every 2 days and filtered through pre-combusted 0.45 μm GF/F, and concentrations of $NO_3^-$—N, $NO_2^-$—N, DOC and cell content are measured.

Figure 7A:
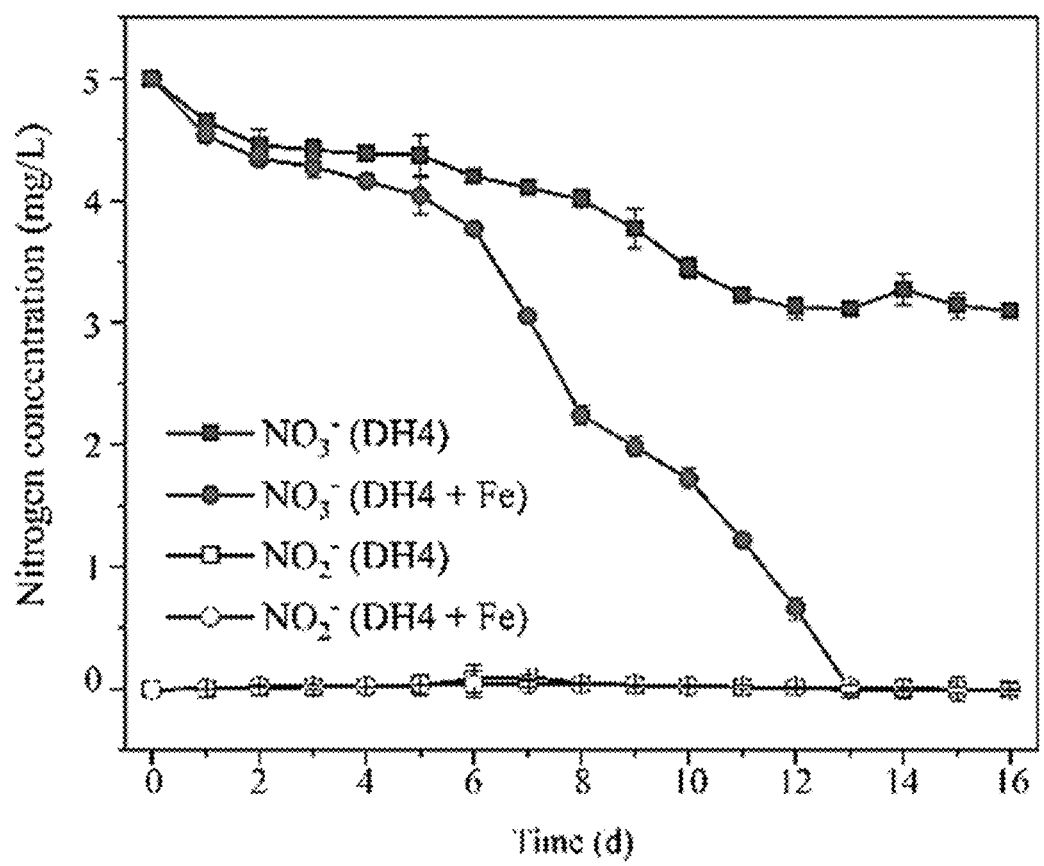
FIG. 7A and FIG. 7B respectively illustrate nitrogen removal performance, and cell growth and dissolved organic carbon (DOC) removal of the *Aspergillus* sp. DH4 of the disclosure under optimal conditions.
Figure 7B:
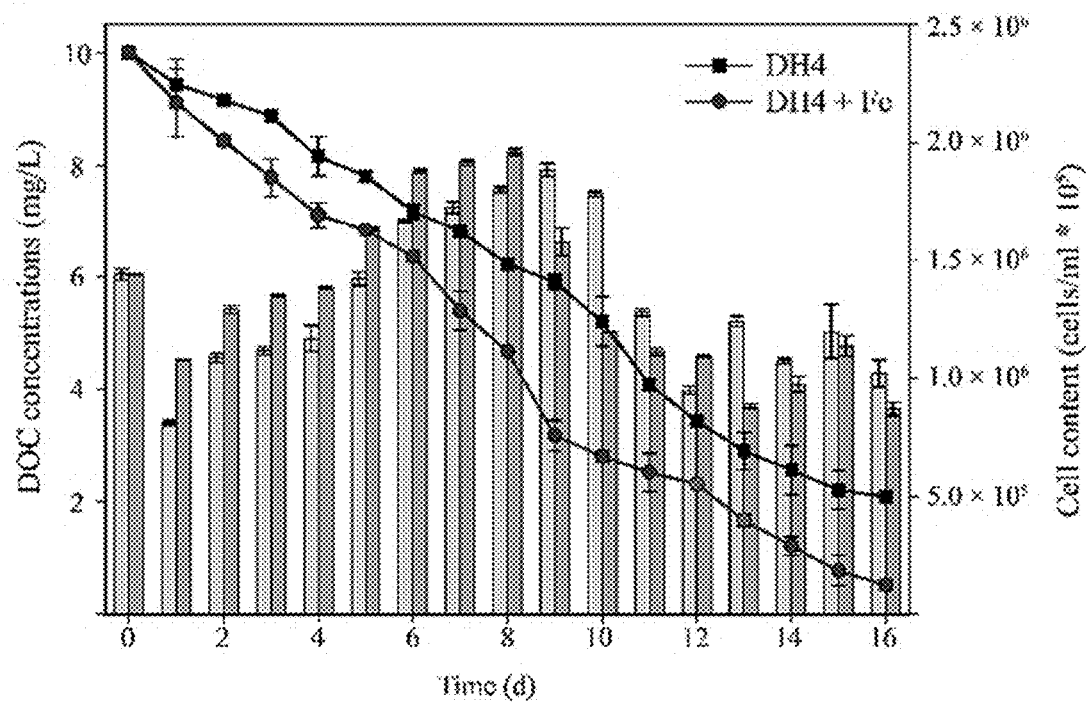

FIG. 7A and FIG. 7B show that without adding electron donors, the initial 0-1 days are an adaptation period, during which the cell count slightly decreases (from $1.54 \times 10^6$ to $9.11 \times 10^5$), and the nitrate removal rate is relatively slow (nitrate concentration decreases from 5 mg/L to 4.65 mg/L). During the logarithmic growth phase of the cells (5-10 days), the nitrate concentration of the *Aspergillus* sp. DH4 decreases from 4.37 mg/L to 3.45 mg/L, and the nitrate removal rate reaches a maximum of 37.80% on the twelfth day, followed by fluctuations.

FIG. 7A and FIG. 7B also show that when adding electron donors, the initial 0-1 days are an adaptation period, during which the cell count slightly decreased (from $1.54 \times 10^6$ to $1.17 \times 10^6$), and the nitrate removal rate is relatively slow (nitrate concentration decreased from 5 mg/L to 2.24 mg/L). During the logarithmic growth phase of the cells (4-8 days), the nitrate concentration of the *Aspergillus* sp. DH4 decreases from 4.16 mg/L to 0.00 mg/L, and the nitrate removal rate reaches 100% on the thirteenth day. Meanwhile, as nitrate is continuously removed, the DOC content also gradually decreases. This phenomenon may be due to the cells consuming DOC for self-replication while providing necessary electron donors for denitrification.

Embodiment 8

The release of $Fe^{3+}$ and $Fe^{2+}$ within the system of the *Aspergillus* sp. DH4 is obtained.

Figure 8:
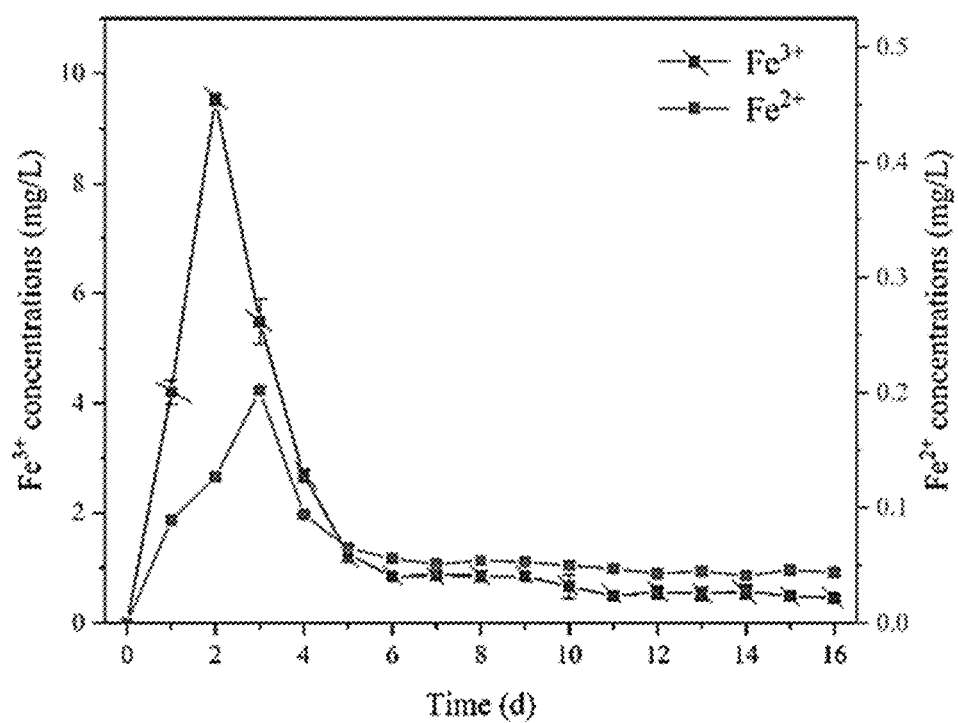
FIG. 8 illustrates release of ferric ions ($Fe^{3+}$) and $Fe^{2+}$ in a system of the *Aspergillus* sp. DH4 of the disclosure.

FIG. 8 shows that in the system of the *Aspergillus* sp. DH4, the concentrations of $Fe^{3+}$ and $Fe^{2+}$ first increases and then decreases. The concentration range of $Fe^{3+}$ is relatively large, reaching a maximum of 1.63 mg/L on the second day, after which it rapidly decreases and fluctuates around 0.60 mg/L. This indicates that the oxidation speed of the iron initially is fast but gradually slows down, with the formation of iron oxides on the surface blocking subsequent iron oxidation, although it continued at a slower pace, leading to the observed fluctuations in concentration. The concentration of $Fe^{2+}$ is relatively low, peaking at 0.20 mg/L on the third day, and then fluctuating within the range of 0.14-0.054 mg/L. The likely reason is that under aerobic conditions, the rate of conversing $Fe^{2+}$ to $Fe^{3+}$ is relatively fast, resulting in a lower concentration of $Fe^{2+}$.

It should be noted that when the claims of the disclosure involve numerical ranges, it should be understood that the two endpoints of each numerical range and any value between the two endpoints can be selected. To avoid repetition, the disclosure describes preferred embodiments.

Although illustrated embodiments of the disclosure have been described, those skilled in the art may make additional changes and amendments to these illustrated embodiments once they have knowledge of the basic inventive concept. Therefore, the appended claims are intended to be interpreted as including the illustrated embodiments and all changes and amendments thereto falling within the scope of protection of the disclosure.

Apparently, those skilled in the art can make various modifications and variations to the disclosure without departing from the spirit and scope of the disclosure. Thus, if these modifications and variations of the disclosure fall within the scope of protection of the appended claims and their equivalent solutions, the disclosure is also intended to include these modifications and variations therein.

What is claimed is:

1. A use of an *Aspergillus* sp. DH4 with aerobic denitrification enhanced by an inorganic electron donor, comprising:

applying the *Aspergillus* sp. DH4 in restoring a nitrogen-containing water body;

wherein the *Aspergillus* sp. DH4 is preserved at China Center for Type Culture Collection (CCTCC), a preservation number is CCTCC NO: M20232690, and a preservation date is Dec. 27, 2023;

wherein the inorganic electron donor is zero-valent iron; and wherein the restoring a nitrogen-containing water body comprises: removing nitrogen from the nitrogen-containing water body.

2. The use as claimed in claim 1, wherein a carbon to nitrogen ratio of the nitrogen-containing water body is in a range of 1-2.5, and a temperature of the nitrogen-containing water body is in a range of 25-30 degrees Celsius (° C.).

3. The use as claimed in claim 1, wherein during the restoring a nitrogen-containing water body, a usage amount of the *Aspergillus* sp. DH4 is 1%-5% of the nitrogen-containing water body in percentages by weight.

4. The use as claimed in claim 1, wherein an added dosage of the zero-valent iron is in a range of 10-15 grams per liter (g/L).

5. The use as claimed in claim 4, wherein the zero-valent iron is a zero-valent iron powder or a zero-valent iron rod.

6. A method for removing nitrate from a polluted water body, comprising:

inoculating the *Aspergillus* sp. DH4 with aerobic denitrification enhanced by the inorganic electron donor as claimed in claim 1 into the nitrogen-containing water body, wherein the zero-valent iron is added as the inorganic electron donor.

* * * * *

SEQUENCE LISTING

```
Sequence total quantity: 1
SEQ ID NO: 1              moltype = DNA   length = 533
FEATURE                   Location/Qualifiers
source                    1..533
                          mol_type = other DNA
                          organism = synthetic construct
SEQUENCE: 1
ctgcggaagg atcattaccg agtgcgggct gcctccgggc gcccaacctc ccacccgtga    60
ctacctaaca ctgttgcttc ggcggggagc cccctagggg cgagccgccg gggaccactg   120
aacttcatgc ctgagagtga tgcagtctga gcctgaatac aaatcagtca aaactttcaa   180
caatggatct cttggttccg gcatcgatga agaacgcagc gaactgcgat aagtaatgtg   240
aattgcagaa ttcagtgaat catcgagtct ttgaacgcac attgcgcccc ctggcattcc   300
gggggcatg cctgtccgag cgtcattgct gccctcaagc ccggcttgtg tgttgggtcg    360
tcgtccccccc cggggacgg gcccgaaagg cagcggcggc accgtgtccg gtcctcgagc    420
gtatgggct ttgtcacccg ctcgattagg gccggccggg cgccagccgg cgtctccaac    480
cttattttttc tcaggttgac ctcggatcag gtagggatac ccgctgaact taa          533
```